United States Patent [19]
Couston

[11] Patent Number: 5,889,279
[45] Date of Patent: Mar. 30, 1999

[54] TUBULAR EVANESCENT WAVE SENSOR FOR MOLECULAR ABSORPTION SPECTROSCOPY

[75] Inventor: Laurent Couston, Les Angles, France

[73] Assignees: Commissariat a l'Energie Atomique, Paris; Compagnie Generale des Matieres Nucleaires, Velizy-Villacoublay, both of France

[21] Appl. No.: 899,649

[22] Filed: Jul. 24, 1997

[30] Foreign Application Priority Data

Aug. 2, 1996 [FR] France ................................ 96 09811

[51] Int. Cl.⁶ ........................................ H01J 5/16
[52] U.S. Cl. ..................... 250/227.25; 250/227.23
[58] Field of Search .................... 250/576, 573, 250/574, 227.23, 227.25; 356/133, 246, 436, 440

[56] References Cited

U.S. PATENT DOCUMENTS

| | | |
|---|---|---|
| 3,557,619 | 1/1971 | Hershler . |
| 4,564,292 | 1/1986 | Omet .................................. 356/133 |
| 4,711,126 | 12/1987 | Houpt et al. ....................... 250/577 |
| 4,844,869 | 7/1989 | Glass ............................... 250/227.25 |
| 4,893,894 | 1/1990 | Caimi . |
| 4,950,885 | 8/1990 | Kershaw ......................... 250/227.25 |
| 5,170,056 | 12/1992 | Berard et al. ..................... 250/341 |
| 5,526,112 | 6/1996 | Sahagen ........................... 250/574 |

*Primary Examiner*—Que T. Le
*Attorney, Agent, or Firm*—Oblon, Spivak, McClelland, Maier & Neustadt, P.C.

[57] ABSTRACT

A sensor including an emission-reception device 22 which emits a light interacting with a fluid 24 and receives the light after it interacts with the fluid. A tubular light guide 26 immersed in fluid has one end facing the emission-reception device and another end for reflection. A structure 32 maintains the tubular light guide at a predetermined distance from the emission-reception device in order to form an evanescent wave in the fluid.

6 Claims, 3 Drawing Sheets

TUBULAR EVANESCENT WAVE SENSOR FOR MOLECULAR ABSORPTION SPECTROSCOPY

BACKGROUND OF THE INVENTION

1. Field of the Invention

The present invention relates to a tubular evanescent wave sensor for molecular absorption spectroscopy. It more particularly applies to the analysis of species in a liquid solution.

2. Discussion of Background

Molecular absorption spectroscopy is an analytical method very frequently used on the laboratory scale. It is based on the selective absorption of light radiation by the species to be analyzed in a solution.

The principles of this method will now be defined. $I_{O,\lambda}$ is the intensity of the incident radiation and $I_{t,\lambda}$ the intensity of the radiation transmitted at wavelength $\lambda$. These two parameters are linked for the formula:

$$I_{T,\lambda} = I_{O,\lambda} 0.10^{-DO}$$

in which DO represents the optical density equal to $\epsilon_\lambda LC$, in which: $\epsilon_\lambda$ is the molar extinction coefficient (expressed in $mol^{-1}$. liter. $cm^{-1}$), L is the optical path in the solution (expressed in cm), and C is the concentration of the chemical species to be analyzed (expressed in $mol.liter^{-1}$).

For spectrophotometers commonly used in the laboratory, the highest measurable optical densities are between 4 and 7 (giving an attenuation of the signal varying between $10^4$ and $10^7$).

Using measuring cells with a reduced optical path L, it is still possible to measure absorbances $\epsilon_\lambda$ C which can reach 100 $cm^{-1}$. Beyond these values, the sample to be analyzed must be diluted, provided that the dilution medium does not disturb the optical properties of the species to be analyzed.

In line analysis by molecular absorption spectroscopy (the term molecular absorption photometry also being used) requires the use of an optical sensor connected to the measuring apparatus by means of two optical fibers. One of the fibers makes it possible to carry the light from the light source of the apparatus up to the measurement point. The other optical fiber makes it possible to collect the transmitted radiation after an optical path of length L in the solution.

As in the case of a laboratory analysis, the optical path is adjusted as a function of the opacity of the solution to be analyzed.

However, when the absorbance is very high (well above 50 $cm^{-1}$), the optical path necessary for the measurement becomes so small that the solution is trapped between the light emitter and the light collector associated with the sensor due to a capillarity phenomenon. Thus, the sensor no longer serves as an inline sensor.

Hereinafter consideration is given to evanescent wave sensors, which are used in absorption measurements of highly absorbant solutions. Their principle is based on the submicron intrusion property of light at the instant of its deviation by a reflecting surface.

The notion of the evanescent wave will be defined. When a light ray coming from a first medium with a refractive index $n_1$ arrives at the surface of a second medium of refractive index $n_2$ lower than $n_1$, the incidence angle $\beta$ of the light ray determines two behaviours of the corresponding electromagnetic wave:

If $\beta$ is lower than a critical angle $\beta_c$, the electromagnetic wave is completely transmitted to the second medium.

If $\beta$ is equal to or greater than $\beta_c$, the electromagnetic wave is completely reflected at the interface between the two media.

The critical angle $\beta_c$ is defined by the following formula:

$$\sin \beta_c = n_2/n_1.$$

From the physical standpoint, the sudden passage from a transmitted wave to a reflected wave is not completely satisfactory.

A more precise study using Maxwell equations introduces a transient stage between these two phenomena using the notion of the evanescent wave.

The modelling of the behaviour of electromagnetic waves at the medium change shows that in the case where $\beta$ is equal to or greater than $\beta_c$, the light slightly penetrates the second medium before being reflected towards the first. This intrusion, whose depth is linked with the wavelength $\lambda$ of the radiation, is known as the "evanescent wave".

The intrusion depth dp is given by the following formula:

$$dp = \frac{\lambda}{2 \cdot \pi \cdot n_1 \cdot \sqrt{(\sin(\beta))^2 - (n_2/n_1)^2}}$$

For wavelengths in the visible range (0.4 to 0.8 $\mu m$), said depth dp is a few micrometers. It is this property which is used in evanescent wave sensors.

The interest of an evanescent wave in analysis will be demonstrated hereinafter. An electromagnetic wave propagates in an optical conductor effecting a plurality of reflections. For each reflection, the surrounding medium is probed by the radiation. It is therefore possible to take advantage of these reflections to produce an optical sensor.

However, the dimensions of the sensor would be highly dependent on the incidence angles of the wave.

A curve illustrating the penetration of a wave as a function of its incidence angle is given in FIG. 1. The incidence angle $\beta$ is plotted on the abscissa and the intrusion depth dp on the ordinate.

Two areas can be observed in FIG. 1 being separated by a value $\beta 1$ of angle $\beta$, which is dependent on the wavelength of the radiation used and the absorbance of the medium probed by the radiation:

an area I, characterized by a high wave penetration, which generates a high reflection level per unit of length of the optical conductor and an area II, characterized by a low wave penetration, which generates a low reflection level per unit of length of the optical conductor.

It is therefore area I which offers the most advantages (small overall dimensions) for implementing a miniature evanescent wave sensor according to the invention, said sensor being intended to function in area I.

However, it is necessary to be able to accurately adjust the propagation angles of the electromagnetic wave.

As soon as it is possible to adjust the propagation angles of an electromagnetic wave in an optical guide, it is possible to control the depths probed at each of the reflections and consequently have the optical guide serving as an optical evanescent wave sensor.

Such depths of approximately 1 $\mu m$ for wavelengths in the visible range open new perspectives to in situ spectrometric analytical methods.

At present numerous laboratories are showing great interest in such sensors. However, the problems of designing such sensors have only been studied to a limited extent.

Two categories of optical evanescent wave sensors or probes are known.

In the first category, diagrammatically illustrated in FIG. 2, the sensors comprise an optical fiber 2 without a protective sheath and placed in a branch circuit 4 in which circulates the solution to be analyzed in the direction indicated by the arrows F. FIG. 2 also shows a light source 6 and a light detector 8 respectively coupled to the ends of the fiber 2.

In the second category diagrammatically illustrated in FIG. 3, the sensors comprise a glass plate 10, whereof one face is immersed in the solution to be analyzed 12.

A longitudinal slot made on the duct 13 in which circulates the solution in accordance with arrows G receives the glass plate 10 in order to permit said immersion. The opposite plate face is provided with two prisms 14 and 16 at its two ends. These are respectively intended to inject the electromagnetic wave into the plate 10 and extract said wave from the plate.

Moreover, these prisms 14 and 16 are respectively coupled to a light source 18 and to a light detector 20.

The sensors shown in FIGS. 2 and 3 are the most widely used on the laboratory scale. However, they are not very suitable for the industrial environment because of the distance separating the light inlet from the outlet, their overall dimensions (for the sensors illustrated in FIG. 2), and the difficulties in implementing and replacing (for the sensors illustrated in FIG. 3).

SUMMARY OF THE INVENTION

The present invention aims at obviating the aforementioned disadvantages. It relates to an evanescent wave sensor for analyzing a fluid (a liquid or a gas) by molecular absorption spectroscopy, said sensor being characterized in that it comprises:

emission-reception means for emitting a light, which is able to interact with the fluid, and receives said light after its interaction with said fluid, a tubular light guide intended to be immersed in the fluid and whereof a first end is positioned facing the emission-reception means and whereof a second end is able to reflect the light propagating in the guide and means for maintaining the guide at a distance from the emission-reception means, said distance permitting the formation of the evanescent wave in the fluid when the light propagates in the guide.

Preferably, the emission-reception means comprise a central optical fiber intended to emit the light, the end of said fibre positioned facing the tubular light guide and the latter being coaxial and peripheral optical fibers surrounding the central optical-fibers and intended to receive the light passing out of the first end of the guide.

According to a preferred embodiment of the sensor according to the invention, the first end of the tubular light guide is chamfered to form a truncated cone, the apex of the corresponding cone being located within the guide.

The chamfer permits the propagation of light in the tubular guide in accordance with angles appropriate for the evanescence of the wave.

Without said chamfer, the distance separating the tubular guide from the emission-reception means (preferably optical fibers) would be too great to envisage the implementation of a reduced size sensor. Thus, said chamfer makes it possible to reduce the distance between the tubular light guide and the emission-reception means.

According to an embodiment, the second end of the tubular light guide is covered with a material able to reflect light.

The holding means can comprise a tubular member containing the first end of the tubular light guide and the end of the emission-reception means facing said first end and means for immobilizing said first end at the said distance within the member.

The sensor can also comprise means for the tight closure of the first and second ends of the tubular light guide and a calibration fluid contained within the tubular light guide. The sensor then has an internal reference.

BRIEF DESCRIPTION OF THE DRAWINGS

The present invention will be better understood from studying the following purely illustrative and non-limitative embodiments described hereinafter with reference to the attached drawings, wherein show.

DETAILED DESCRIPTION OF EMBODIMENTS

Figure 1:
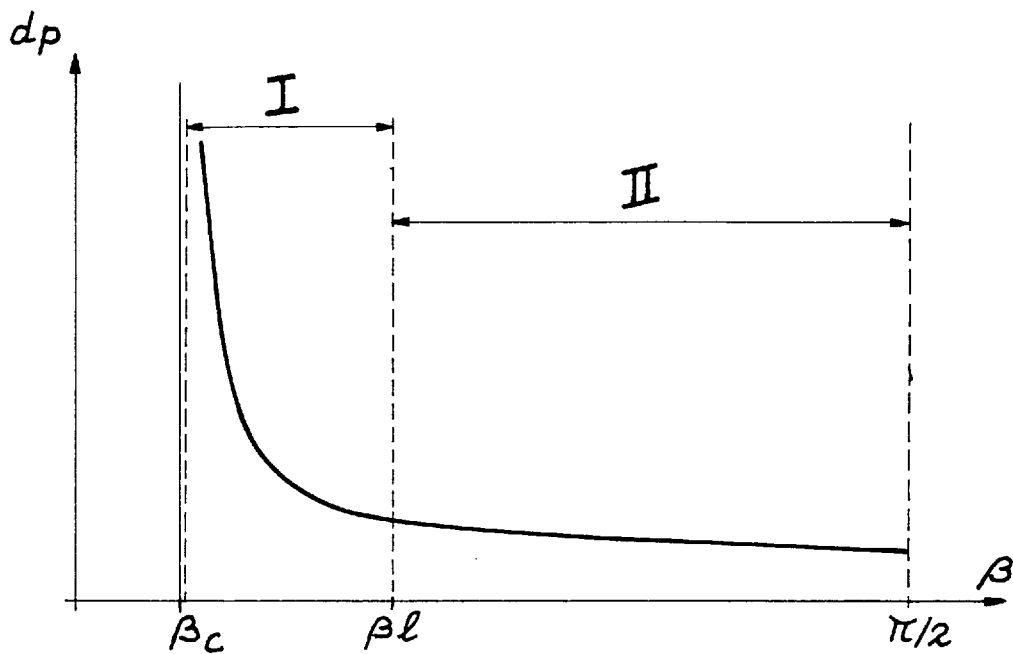
FIG. 1, already described, variations of the intrusion depth dp of an electromagnetic wave in a medium, as a function of the incidence angle β of the wave, at the interface between said medium and another medium where the wave propagates.
Figure 2:
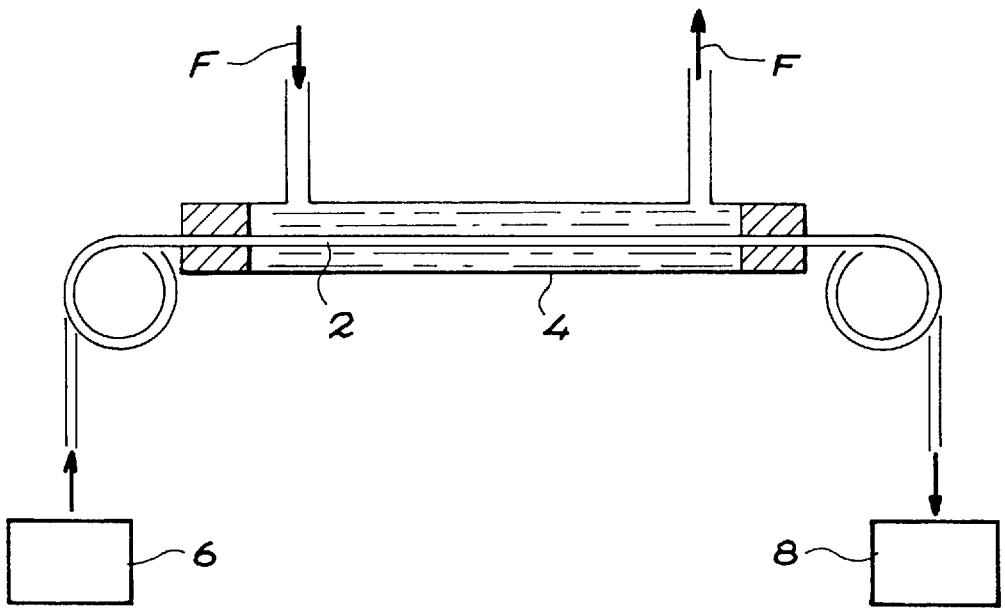
FIGS. 2 and 3, already described, diagrammatically known evanescent wave sensors.
Figure 3:
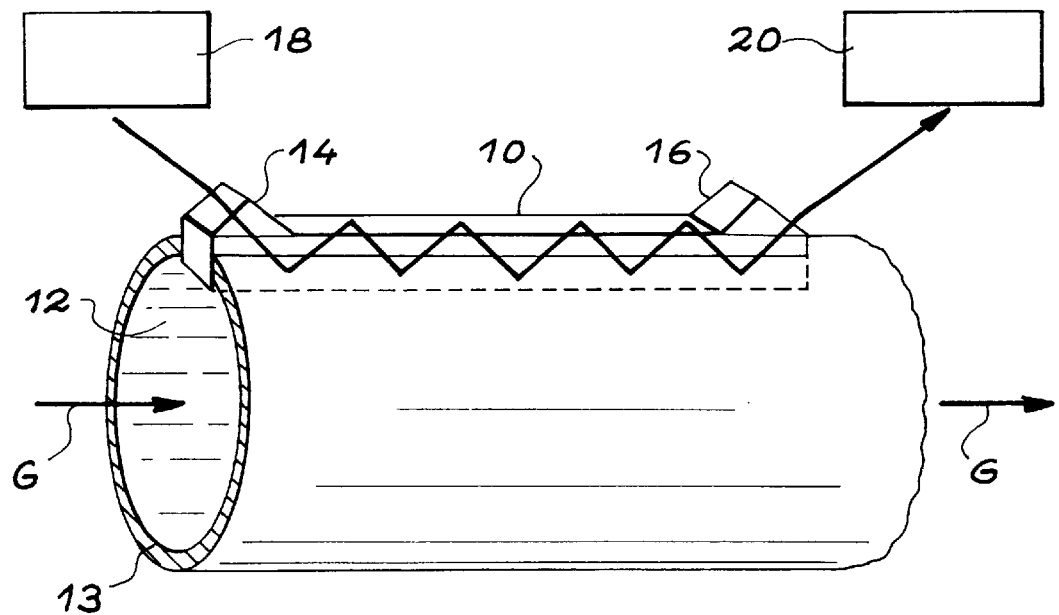
Figure 4:
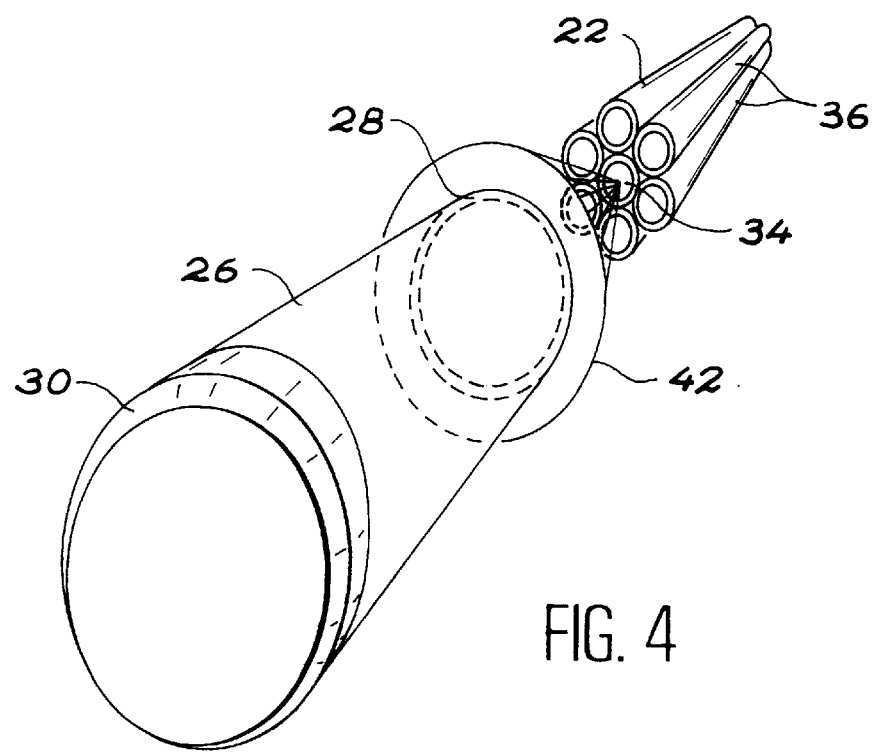
FIG. 4 A diagrammatic partial perspective view of an embodiment of a sensor according to the invention.
Figure 5:
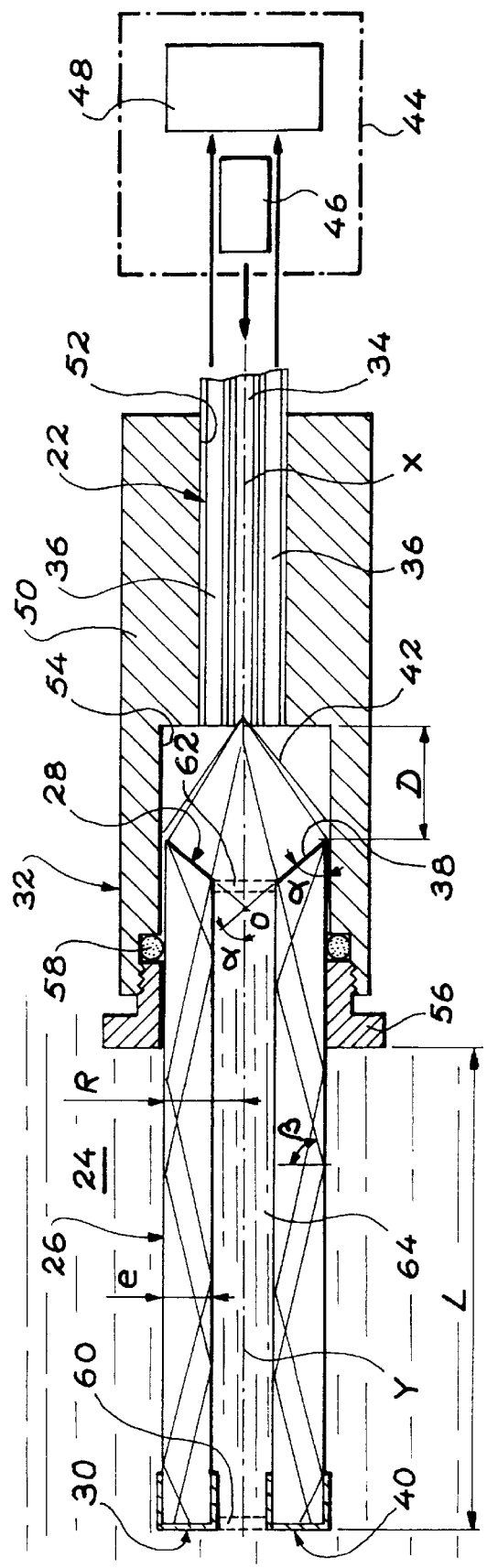
FIG. 5 A diagrammatic, longitudinal sectional view of the sensor of FIG. 4.

The sensor according to the invention diagrammatically shown in FIGS. 4 and 5 comprises:

emission-reception means 22 for emitting a light able to interact with a liquid solution 24, which it is wished to analyze by molecular absorption spectroscopy with said sensor and to receive said light after the interaction thereof with the liquid, a tubular light guide 26, e.g. of glass, which is to be immersed in the liquid and whereof a first end 28 is positioned facing emission-reception means 22 and whereof a second end 30 is able to reflect the light propagating in the guide and means 32 for maintaining the guide at a distance D from said emission-reception means 22, said distance permitting the formation of an evanescent wave in the liquid 24 when the light propagates in the guide 26.

In the represented embodiment, the emission-reception means 22 incorporate a bundle of optical fibers having a central optical fiber 34 for emitting the light and peripheral optical fibers 36 surrounding the central optical fiber 34 and which the light passing out of the first end 28 of the guide 26.

The axis X of the end of the fiber 34 facing the tubular guide coincides with the axis Y of the latter. At said end, the axes of the fibers 36 are parallel to the axis of the fiber 34.

The first end 28 of the tubular light guide 26 is provided with a chamfer 38 so as to form a truncated cone, the apex O of the corresponding cone being within the tubular light guide 26 on the axis Y.

The second end 30 of the tubular light guide 26 is covered with a layer 40 of a material able to reflect light, so that said layer 40 forms a mirror at the end 30 of the light guide 26.

FIGS. 4 and 5 also show the conical light beam 42 from the central optical fiber 34 and in which is located the end 28 of the guide 26.

FIG. 5 also diagrammatically shows a measuring apparatus 44 permitting the performance of the molecular absorption spectroscopy and the provision of the corresponding measurements for users.

The apparatus 44 comprises a laser source 46, which produces the light transmitted by the central fiber 34 and a measuring device 48 which receives the light from the peripheral optical fibers 36.

Not shown means permit an optical coupling between the source 46 and the central fiber 34 and between the device 48 and the peripheral fibers 36.

Thus, the light emitted by the laser source propagates in the central fiber and passes out of the latter in the form of the light beam 42, in which is placed the end 28 of the tubular guide 26.

Part of the beam 42 penetrates the guide by the chamfered end 28 thereof and propagates therein with the aid of successive reflections. An evanescent wave forms in the liquid 24.

The light propagating in the guide is reflected by the mirror 40 and passes into the peripheral fibers 36 and is then analyzed by the device 48.

The angle $\beta$ of light propagation in the tubular guide 26 slightly exceeds the critical angle $\beta_c$, so that it is in the aforementioned area I. This angle $\beta$ is adjusted by varying the distance D between the central optical fiber 34 and the large base of the truncated cone formed by the chamfer 38. The semiangle at the apex of the corresponding cone is designated $\alpha$.

The distance D corresponding to the chamfered tubular guide and making it possible to obtain an evanescent wave is well below the distance corresponding to an unchamfered tubular guide.

In the tubular guide 26, the light is guided up to the reflecting end 30. The material covering said end is a silica-coated aluminium deposit, which totally reflects the light wave. The light then returns to the chamfered end of the tubular guide.

On passing or clearing said chamfered end, the light passes out of the tubular guide and forms a circular image having as its centre the axis Y of said tubular guide. The diameter of said image is roughly equal to twice the thickness e of the tubular guide.

The depth of penetration of the light wave in the liquid is defined by the number of reflections of the light beam in the tubular guide. This number is a function of the thickness e of the tubular guide and the length L of the tubular guide part located in the liquid.

The holding or maintaining means 32 comprise a tight, tubular element 50 visible in FIG. 5. Said element 50 comprises on a first side a first hole 52 for receiving the end of the optical fiber bundle and which faces the tubular guide 26. Said element 50 also has on a second side a second hole 54 for receiving the chamfered end of the tubular guide 26.

As can be seen in FIG. 5, said two holes are coaxial and communicate with one another.

The external diameter 2R of the tubular guide exceeds the diameter of the optical fiber bundle. The diameter of the second hole of the element 50 consequently exceeds the diameter of its first hole.

At the second side and in front of the second hole, the element 50 is provided with an internal thread and the holding means 52 have a tight, externally threaded ring 56, which can be screwed into the threaded portion of said second hole and which is traversed by the tubular guide 26.

An O-ring 58 is placed between said ring and an inner shoulder of the element 50, formed between its thread and the second hole 54, so that the O-ring can be compressed by screwing the ring 32.

This O-ring maintains the sealing of the interior of the element 50 when the tubular guide is immersed in the liquid and, by deformation resulting from the compression, also permits the immobilization of the chamfered end of the tubular guide in said element, at the chosen distance with respect to the end of the central optical fiber 34.

The sensor according to the invention is suitable for the measurement of solutions having high optical densities.

This sensor has four advantages compared with the known evanescent wave sensors referred to hereinbefore. The sensor can have small overall dimensions, namely a length of approximately 15 cm and an external diameter of approximately 1 cm. The entry of the radiation and the exit of the signal take place on the same side of said sensor. An inline positioning of said sensor is possible and it consequently does not have to be placed on a branched flow. The hollow part of the tubular guide can be sealed and filled with a liquid calibration solution. In this case, the sensor has an internal reference.

This possibility is diagrammatically illustrated in FIG. 5, where it is possible to see two plugs 60 and 62 respectively sealing the two ends of the tubular guide. The interior of the latter is filled with a liquid solution 64 constituting a measurement standard.

Hereinafter formulas will be given permitting the optimization of the distance D making it possible to obtain evanescent waves with the tubular guide 26. The distance D is chosen in the range defined by the values $D_1$ and $D_2$, which are a function of the sensitivity required for the measurement to be made.

These values $D_1$ and $D_2$ are given by the following formulas:

$$D_1 = \frac{\phi/2 + R}{tg\beta_c}$$

$$D_2 = \frac{R - \phi/2 - e(1 + (tg\beta_c/tg\alpha))}{tg\beta_c}$$

in which o represents the diameter of the optical sheath of the central optical fiber 34 and $\beta_c$ represents the limiting light propagation angle in the tubular guide, said angle being defined by:

$$\sin \beta_c = n_l/n_g$$

where $n_l$ represents the refractive index of the liquid solution 24 and $n_g$ the refractive index of the light-transparent material forming the tubular light guide.

I claim:

1. An evanescent wave sensor for analyzing a fluid by molecular absorption spectroscopy, said sensor comprising:

emission-reception means for emitting a light which interacts the fluid and for receiving said light after interaction of said light with said fluid;

a tubular light guide immersed in said fluid wherein said tubular light guide has a first end positioned to face the emission-reception means and a second end for reflecting light propagated in said tubular light guide;

means for maintaining said tubular light guide at a predetermined distance from said emission-reception means in order to permit formation of an evanescent wave in the fluid when the light propagates in the tubular light guide.

2. Sensor according to claim 1, wherein the emission-reception means comprise:

a central optical fiber for emitting light, the end of said fiber located facing the tubular light guide and being coaxial with said light guide and peripheral optical fibers (36), which surround the central optical fiber and receive the light passing out of the first end of the guide.

3. Sensor according to claim 1, wherein the first end of the tubular light guide is chamfered to form a truncated cone, the apex (0) of the corresponding cone being within the guide.

4. Sensor according to claim 1, wherein the second end of the tubular light guide is covered with a light reflecting material.

5. Sensor according to claim 1, wherein the maintaining means comprise:

a tubular member containing the first end of the tubular light guide and an end of the emission-reception means positioned facing said first end and means for immobilizing said first end at the said distance within the member.

6. Sensor according to claim 1, therefore further comprising;

means for the tight sealing of the first and second ends of the tubular light guide and a calibration fluid contained in said tubular light guide, so that said sensor has an internal reference.

* * * * *